(12) United States Patent
Schwei et al.

(10) Patent No.: US 7,516,967 B2
(45) Date of Patent: Apr. 14, 2009

(54) CART SANITIZING SYSTEM

(75) Inventors: Mark C. Schwei, Greenville, WI (US); Jeffrey J. Taylor, Green Bay, WI (US); Robert J. Weyers, Green Bay, WI (US)

(73) Assignee: PureCart Systems, LLC, Green Bay, WI (US)

( * ) Notice: Subject to any disclaimer, the term of this patent is extended or adjusted under 35 U.S.C. 154(b) by 348 days.

(21) Appl. No.: 11/062,785

(22) Filed: Feb. 22, 2005

(65) Prior Publication Data

US 2005/0214159 A1 Sep. 29, 2005

Related U.S. Application Data

(60) Provisional application No. 60/547,309, filed on Feb. 24, 2004.

(51) Int. Cl.
*B08B 3/02* (2006.01)
*B62B 3/02* (2006.01)

(52) U.S. Cl. ............. 280/79.2; 280/33.992; 134/15

(58) Field of Classification Search ............ 280/33.992, 280/33.991
See application file for complete search history.

(56) References Cited

U.S. PATENT DOCUMENTS

| | | | |
|---|---|---|---|
| 3,444,867 A | 5/1969 | Thornton | |
| 3,698,029 A | 10/1972 | Pulliam | |
| 3,874,302 A | * | 4/1975 | Crosswhite ............... 104/172.3 |
| 4,807,319 A | 2/1989 | Poitevin | |
| 5,133,375 A | 7/1992 | Schinzing et al. | |
| 5,285,802 A | 2/1994 | Soderquist | |
| 6,090,218 A | 7/2000 | Brackmann et al. | |
| 6,427,707 B1 | 8/2002 | Morris | |
| 6,714,837 B1 | 3/2004 | Brackmann et al. | |

* cited by examiner

*Primary Examiner*—Christopher P Ellis
*Assistant Examiner*—Bridget Avery
(74) *Attorney, Agent, or Firm*—Andrus, Sceales, Starke & Sawall, LLP (57) ABSTRACT

A cart sanitizing system is disclosed for applying a sanitizing fluid to sanitize a shopping cart. A pressurized supply of sanitizing fluid is applied to the cart contained within a cart enclosure through a series of spray nozzles mounted along a spray arch. The pressurized sanitizing fluid is supplied to the spray arch from a pressure tank, which is fed with the supply of sanitizing fluid from a chemical make-down system. The chemical make-down system creates the sanitizing fluid, which preferably includes a sanitizing agent and a surfactant mixed within fresh water. The sanitizing fluid is created by a mixing device by flowing the fresh water over inlet tubes for both the sanitizing agent and the surfactant. The mixture of the surfactant and sanitizing agent allows the sanitizing fluid to be applied to the shopping carts and eliminates the requirement for drying.

18 Claims, 7 Drawing Sheets

CART SANITIZING SYSTEM

CROSS REFERENCE TO RELATED APPLICATION

The present application is based on and claims priority to U.S. Provisional Patent Application Ser. No. 60/547,309, filed on Feb. 24, 2004.

BACKGROUND OF THE INVENTION

The present invention generally relates to a system and method for sanitizing shopping carts and other similar devices. More specifically, the present invention relates to a mobile, self-contained system that sanitizes shopping carts utilizing a sanitizing fluid that does not need to be rinsed from the shopping cart and dries quickly.

Presently, supermarkets, grocery stores and similar shopping establishments provide shopping carts for the customer's convenience. The carts are adapted to hold the customer's selected purchases and thus often contain food, including liquids, which at times are spilled or come in contact with the cart surfaces. Additionally, many of the customers using the shopping carts have small children who are carried in the carts. These small children often place their mouths and hands on the shopping cart handles. Recently, numerous studies have been published that indicate that a large amount of bacteria and microorganisms exist on the handles and other areas of shopping carts.

Clearly, it is recognized as good sanitation practice to have shopping carts cleaned at regular periodic intervals to reduce the levels of microorganisms and bacteria that are living on the areas of the shopping cart that come into contact with a customer. Presently, federal reports have been generated that highlight the amount of bacteria and microorganisms existing on grocery carts. Failure to thoroughly clean such shopping carts could reduce the level of customers to a particular store in the future if customers are alerted to the presence of unsanitary, soiled carts at the store. Likewise, if a store periodically cleaned and sanitized the shopping carts, the store could advertise such a fact, which would greatly enhance the customer comfort level and eventually business at the store.

The standard practice at most stores that utilize shopping carts is to very infrequently clean the shopping carts manually by the use of a high pressure hot water wand including a detergent. Once the detergent is applied to the shopping cart, a hot water rinse is used to remove the detergent from the shopping carts. Unfortunately, the manual washing of carts is inefficient since it requires a great deal of paid employee time to wash the numerous carts present at a store. Further, the use of high pressure washing equipment and detergent creates a mess in the parking lot of the store, which makes the manual washing of the shopping carts even more undesirable.

Presently, several systems exist that provide for a automatic shopping cart washing system that somewhat automate the process, thereby eliminating the need for total manual washing of the shopping carts. Examples of such automated wash systems are set forth below.

U.S. Pat. No. 5,993,739 relates to a method for cleaning objects such as wheel chairs on a continuous basis. The invention is a mobile, self-contained system in which objects are cleaned and sanitized as they travel in a U-shaped path within a wash chamber. As the objects enter the first side of the wash chamber, suitably located water jets spray the objects with a mixture of detergent and water to remove associated foreign materials until shortly after the objects make a U-turn. At this point, the objects are first sprayed with a mixture containing a rinse agent and water, then with a spray containing disinfectant and water. The objects are then dried by suitable drying means, such as a high velocity air curtains system.

U.S. Pat. No. 5,133,375 relates to a washer for a conventional wheelchair having a washing chamber within an enclosure with fluid-driven rotatable washer arms having suitably angled nozzles for directing cleaning and rinsing fluids onto a wheelchair mounted on a slidable rack just above the slanted drain floor of the enclosure.

U.S. Pat. No. 5,285,802 relates to a portable wheelchair cleaning apparatus. The system includes a modular assembly having a washing chamber, operators control unit, and a mobile base support structure housing the electromechanical components used to apply the cleaning process. The operator places a wheelchair in the wash chamber and from the control unit selects cleaning functions to be applied through a programmable micro-processor. A pump draws cleaning solution from the sink through a line connected to the rotating spray arm assembly. As the spray arm lifts past the wheelchair, the solution is sprayed against the wheelchair through nozzles on the spray arm. The solution returns into the sink for continuous re-cycling. A drain pump draws the contaminated water from the sink through a drain line into a drain receptacle when the wash and rinse cycle are completed.

U.S. Pat. No. 5,622,196 relates to an apparatus for washing objects comprising a frame supporting a housing dimensioned to receive various irregularly shaped objects. A conveyor belt having exterior sections that extend beyond the housing entrance and exit, conveys the objects through the housing as a first series of nozzles spray the objects with a cleaning solution. Then, the objects are washed by a pair of high speed rotating spray arms, mounted on the exterior sides of the housing, which direct pressurized water through circular cut out portions formed in the sides of the housing to the objects being conveyed through the housing. The objects are then rinsed by a second series of nozzles and subsequently exit the housing. The exterior sections of the conveyor belt are rotatable and are rotated toward the housing to form a compact configuration for transportation and storage.

Therefore, a current need exists for a sanitizing system that effectively reduces the levels of bacteria and microorganisms on shopping carts that can be operated relatively quickly and easily by minimal personnel to reduce the cost of operation. A further need exists for a cart sanitizing system that is compact in size, easily movable and minimizes the capital expenditure required by the owner.

SUMMARY OF THE INVENTION

The present invention relates to a method and apparatus for applying a sanitizing fluid to a shopping cart such that the shopping cart can be sanitized. The mobile sanitizing system of the invention allows a shopping cart to be quickly and easily sanitized without requiring time consuming drying and rinsing procedures.

The sanitizing system includes a cart enclosure designed to receive the shopping cart being cleaned. Preferably, the cart enclosure is slightly larger than the size of a typical shopping cart such that the entire shopping cart can be contained within the cart enclosure. The cart enclosure includes a floor, a pair of spaced side walls, a first end wall having an entrance and a second end wall having an exit. Both the first and second end walls preferably include a flexible mist guard that reduces the amount of spray leaving the cart enclosure.

The cart enclosure includes an entrance ramp and an exit ramp, each of which are movable between a loading position and a storage position. When the entrance and exit ramps are in the loading position, each entrance ramp extends from the floor of the cart enclosure to the ground, which allows a shopping cart to be rolled into the cart enclosure. When the entrance and exit ramps are moved to their respective storage positions, the cart enclosure can be easily moved. Preferably, the cart enclosure includes at least a pair of caster wheels positioned near the entrance to the cart enclosure. The opposite end of the cart enclosure includes a pair of non-skid pads that stabilize the cart enclosure in its desired location.

The cart enclosure includes a spray arch positioned within the enclosure between the entrance and the exit. The spray arch includes multiple nozzles spaced around the arch, including a floor-mounted nozzle, to provide complete spray coverage when a shopping cart is beneath the spray arch. The spray arch is in fluid communication with a source of pressurized sanitizing fluid such that the sanitizing fluid can be sprayed onto the shopping cart through the spray nozzles. Preferably, each of the spray nozzles includes a diaphragm check valve such that the check valves prevent a discharge of sanitizing fluid when the pressure of the fluid supplied to the nozzles falls below a threshold pressure.

The sanitizing system includes a motion detector mounted within the enclosure that detects the movement of the shopping cart into the enclosure through the entrance. Upon detection of the shopping cart, a control valve is opened to supply the pressurized sanitizing fluid to the spray arch. Preferably, the sanitizing system includes a timer that monitors the duration of time that has expired since the motion detector detected the entrance of a shopping cart into the cart enclosure. After the expiration of a spray period, the timer closes the control valve, which prevents the further discharge of sanitizing fluid through the spray nozzle of the spray arch. When the next shopping cart is moved into the cart enclosure, the motion detector again opens the control valve to begin spraying the sanitizing fluid.

The pressurized sanitizing fluid is supplied to the spray arch from a pressure tank coupled to the spray arch through the control valve. The pressure tank includes a supply of sanitizing liquid at a desired pressure. The pressure within the pressure tank is created by a pump positioned between a supply tank and the pressure tank. When the pressure within the pressure tank falls below a minimum value, the pump introduces an additional supply of the sanitizing fluid into the pressure tank from the supply tank. In this manner, the pressure pump maintains the pressure within the pressure tank by supplying an additional sanitizing fluid.

The supply tank coupled to the pressure pump stores a supply of sanitizing fluid that is created through a chemical make-down system. The chemical make-down system mixes a desired supply of a surfactant and a desired supply of a sanitizing agent into a flow of fresh water to create the sanitizing fluid. The sanitizing agent within the sanitizing fluid allows the sanitizing fluid to sanitize the shopping cart while the surfactant reduces the surface tension of the water, which aids in the rapid drying of the shopping cart after the sanitizing fluid has been applied.

Preferably, the mixing device includes a surfactant inlet tube and a chemical inlet tube each having an inlet opening extending into a flow of fresh water. As the fresh water passes over the inlet openings for both the surfactant tube and the chemical tube, the flow of water draws both the surfactant and the sanitizing agent into the flow of water. The amount of surfactant and sanitizing agent drawn into the flow of water is dictated by the size of each of the respective inlet openings. The sanitizing liquid created by the chemical make-down system is stored in the supply tank. The supply tank includes multiple level sensors that maintain the volume of sanitizing fluid in the supply tank between an upper level and a lower level where the stored supply of sanitizing fluid is created by the mixing device.

The cart enclosure of the sanitizing system includes a drain formed in the floor of the cart enclosure. The drain includes a discharge tube used to direct the sanitizing fluid applied to the shopping cart to a location remote from the shopping cart enclosure. Preferably, the discharge tube is used to direct the used sanitizing fluid to a drain or sewer.

The sanitizing system includes a pair of adjustable guide rails contained on both the entrance ramp and the exit ramp. The guide rails aid in directing the shopping carts into the shopping cart enclosure. The guide rails are particularly desirable when shopping carts are being fed into the cart enclosure in a nested arrangement.

BRIEF DESCRIPTION OF THE DRAWINGS

The drawings illustrated the best mode contemplated of carrying out the invention. In the drawings.

DETAILED DESCRIPTION OF THE PREFERRED EMBODIMENT

Figure 1:
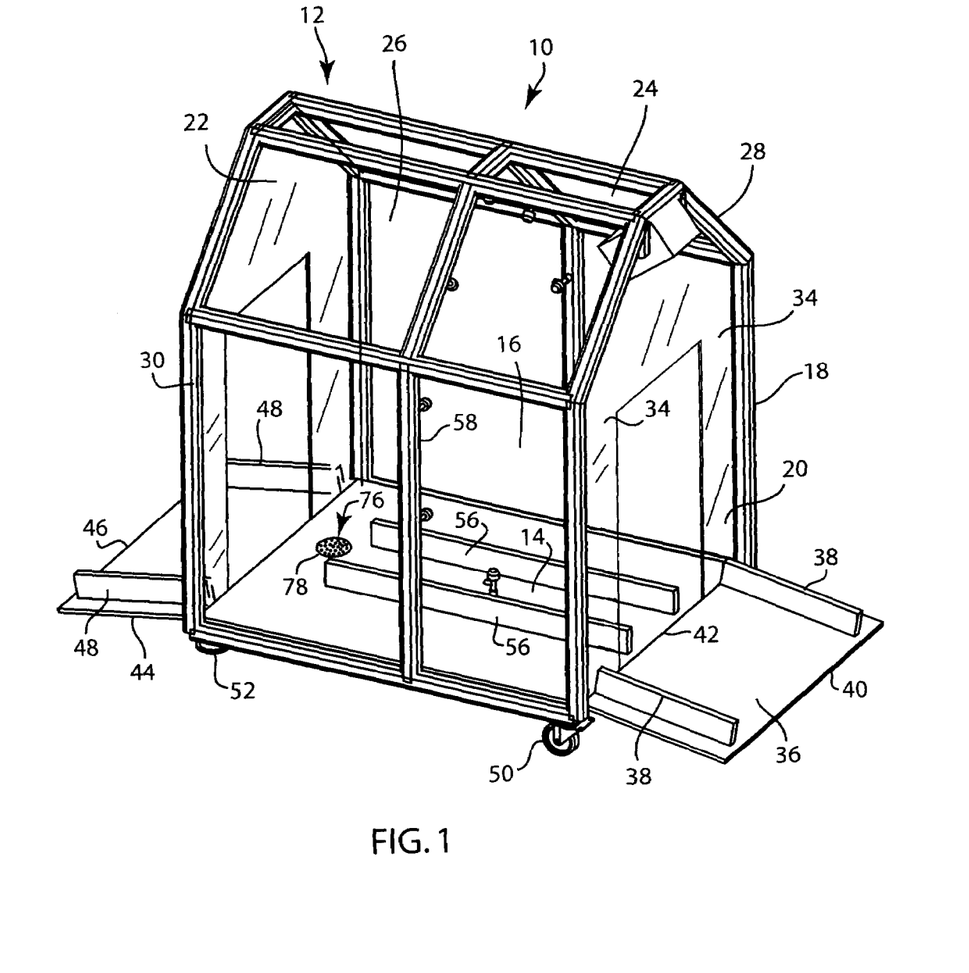
FIG. 1 is a perspective view of the shopping cart sanitizing system of the present invention.

Referring first to FIG. 1, there shown is a cart sanitizing system 10 of the present invention. The cart sanitizing system 10 is configured to receive one or more shopping carts and apply a sanitizing fluid to the shopping carts to substantially reduce the number of microorganisms and bacteria present on the shopping cart. Throughout the following description, the cart sanitizing system is described as sanitizing a shopping cart. The term sanitizing refers to substantially reducing the number of microorganisms and bacteria and does not require the complete elimination of such organisms. The cart sanitizing system 10 generally includes a cart enclosure 12 having a floor 14, a pair of spaced side walls 16,18, a first end wall 20 and a second end wall 22. The top of the cart enclosure 12 includes a top wall 24 and a pair of angled supporting walls 26,28.

In the embodiment of the invention illustrated in FIG. 1, each of the walls of the cart enclosure 12 are formed from a clear, polycarbonate material supported by a series of aluminum support beams 30. However, it is contemplated by the inventors that the polycarbonate panels and aluminum support beams could be replaced by a unitary, molded enclosure while operating within the scope of the invention. The materials utilized to create the cart enclosure 12 are shown and described in the present application as one embodiment of the invention and are not meant to limit the scope of protection to which the inventors are entitled.

The first end wall 20 defines an entrance 32 bounded on each of its sides by a flexible mist guard 34. The mist guard 34 reduces the amount of mist that leaves the cart enclosure 12 from the generally open interior. The shopping cart enclosure 12 includes an entrance ramp 36 movable between a storage position and a loading position, as shown by arrow 37 in FIG. 2. As shown in FIG. 1, when the entrance ramp 36 is in its loading position, the entrance ramp 36 contacts the ground or floor and provides a ramp for a shopping cart to be pushed upward through the entrance 32 and onto the floor 14 of the enclosure 12. As illustrated, the entrance ramp 36 includes a pair of spaced guide rails 38 that taper inward from the bottom edge 40 to the top edge 42 of the entrance ramp. The guide rails 38 act to center a shopping cart along a central axis of the cart enclosure 12. The guide rails 38 are particularly desirable when a nested stack of carts are being pushed into the cart enclosure 12. Each of the guide rails 38 is adjustable such that the distance between the guide rails 38 at the top edge 42 of the entrance ramp 46 can be varied depending upon the type of shopping cart being sanitized.

The shopping cart enclosure 12 further includes an exit ramp 44 mounted to the enclosure 12 near the second end wall 22. As shown by arrow 45 in FIG. 2, the exit ramp 44 is movable between a loading position in which the bottom edge 46 contacts the floor or ground and a storage position. As shown in FIG. 1, the exit ramp 44 includes a pair of spaced guide rails 48 that can be adjusted depending upon the width of the carts being sanitized.

Figure 2:
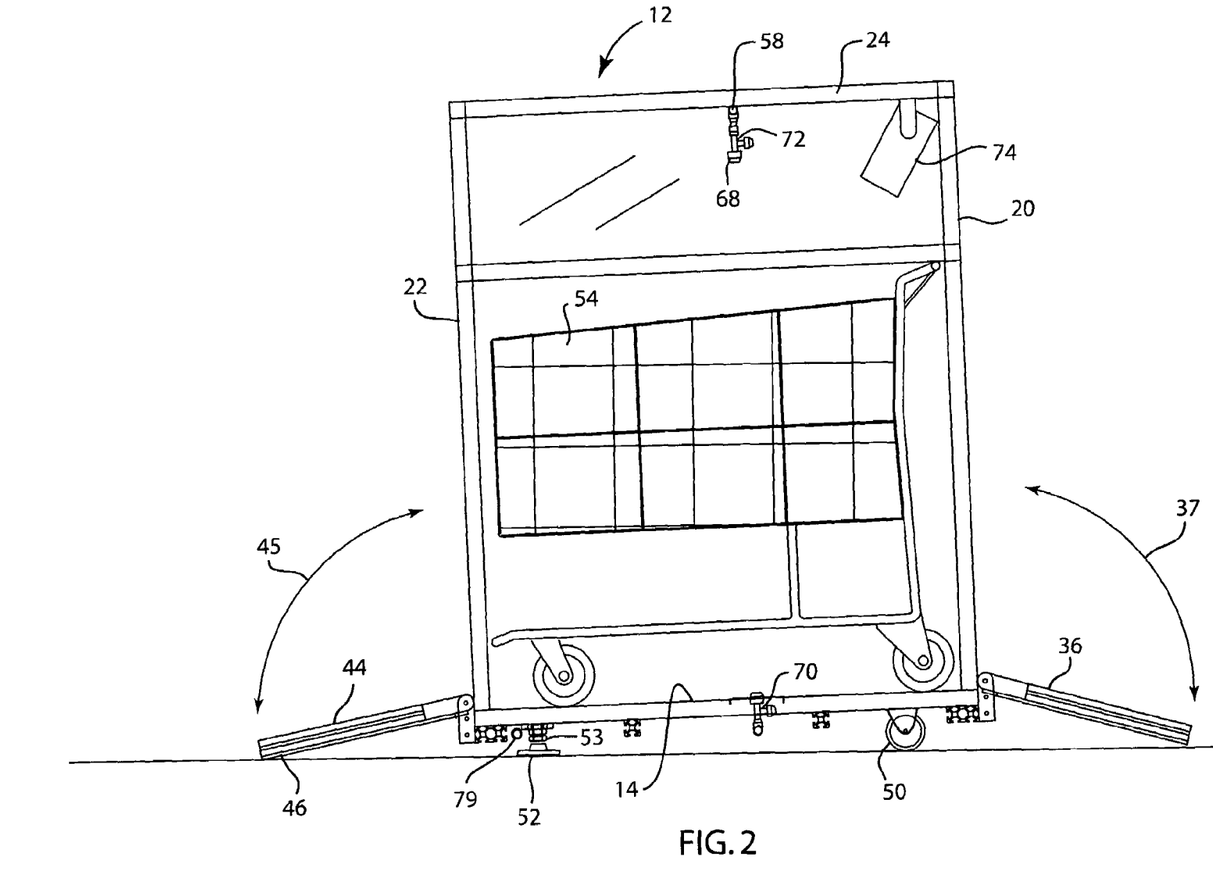
FIG. 2 is a side view of the sanitizing system shown in FIG. 1.
Figure 3:
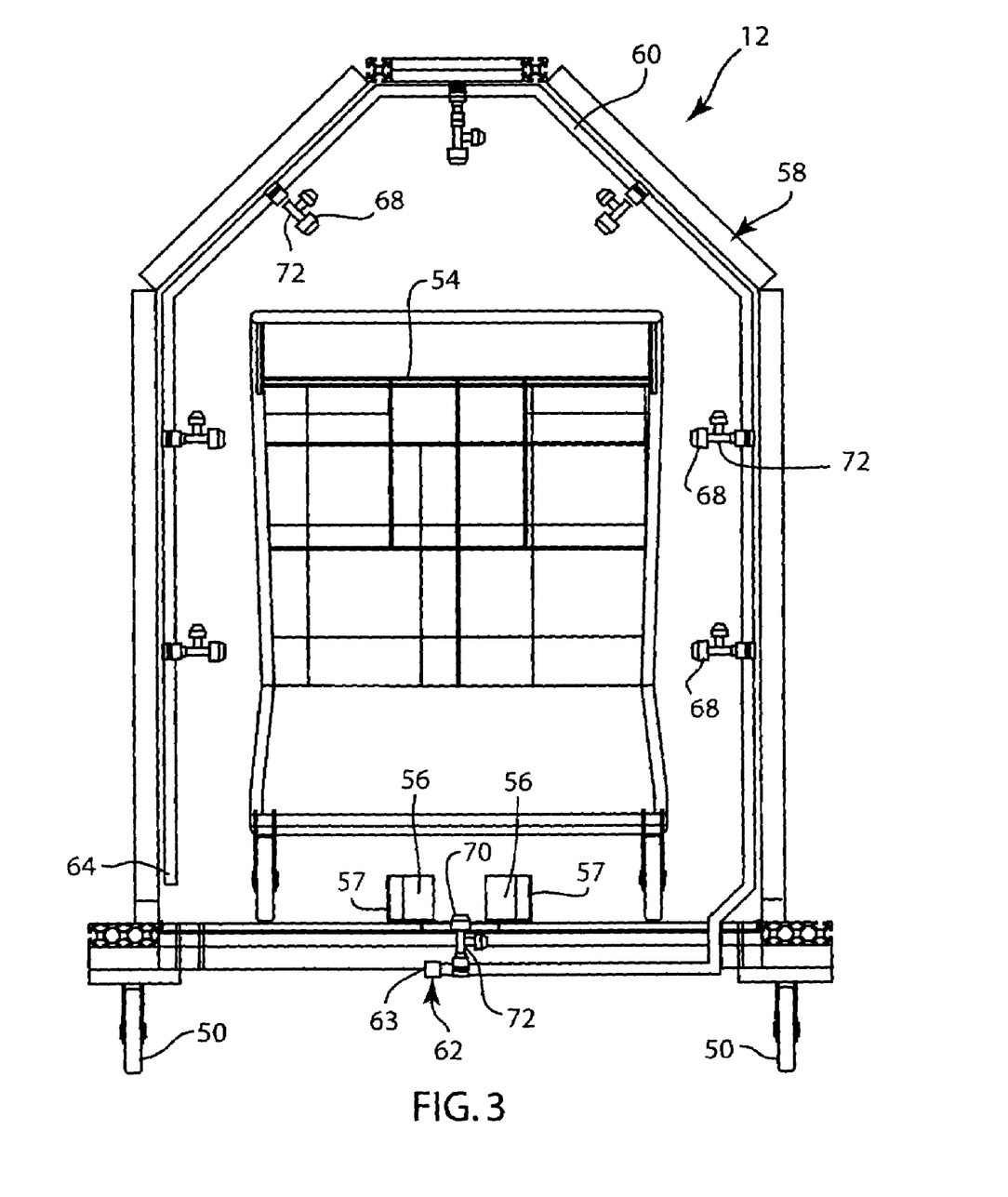
FIG. 3 is an end view of the sanitizing system shown in FIG. 1.

Referring now to FIGS. 1-3, the cart enclosure 12 includes a pair of caster wheels 50 mounted near the entrance to the cart enclosure. The caster wheels 50 are mounted below the floor of the cart enclosure and allows the cart enclosure 12 to be moved as desired.

The exit end of the cart enclosure 12 preferably includes a pair of spaced non-skid pads 52. The non-skid pads 52 are each mounted to an adjustment mechanism 53 so that the height of the exit end of the cart enclosure can be adjusted. As can best be seen in FIG. 2, the floor 14 slopes downward from the entrance end to the exit end of the cart enclosure 12. The sloping floor 14 aids in encouraging each of the shopping carts 54 to roll from the entrance opening to the exit opening.

Referring now to FIG. 3, the cart enclosure 12 includes a pair of centering bars 56 mounted to the floor 14 of the cart enclosure. The centering bars 56 contact the front wheels of the shopping carts to aid in guiding the shopping cart 54 through the cart enclosure 12. The distance between the outer edges 57 of the centering bars 56 is adjustable depending upon the type of shopping cart 54 being sanitized.

The cart enclosure 12 includes a spray arch 58 that is spaced slightly inward of the outer walls of the cart enclosure. As best shown in FIG. 2, the spray arch 58 is positioned between the first end wall 20 and the second end wall 22 of the cart enclosure 12. Referring back to FIG. 3, the spray arch 58 includes a fluid conduit 60 that extends from an inlet end 62 to the termination end 64. The inlet end 62 includes an end fitting 63 that connects the fluid conduit 60 to a supply source for the sanitizing fluid. In the embodiment of the invention illustrated, the fluid conduit 60 is formed from PVC, although other materials are contemplated as being within the scope of the invention.

The spray arch 58 includes a series of nozzles 68 spaced along the length of the spray arch. As best seen in FIG. 3, the spray arch 58 includes seven individual nozzles 68 spaced around the shopping cart 54 when the shopping cart is positioned within the shopping cart enclosure 12. In addition to the seven nozzles 68 spaced around the shopping cart, the sanitizing system includes a floor mounted nozzle 70. The combination of the seven nozzles 68 and the floor mounted nozzle 70 provide a complete spray pattern that covers the entire shopping cart 54 when the shopping cart 54 passes beneath the spray arch 58.

In the embodiment of the invention illustrated in the figures, each of the spray nozzles 68 is coupled to the fluid conduit 60 by a nozzle body 72 that includes a diaphragm check valve. In operation, the check valve of the nozzle body 72 allows fluid to reach the spray nozzle 68 only when the pressure of the fluid being distributed exceeds a threshold pressure. In the embodiment of the invention illustrated, the diaphragm check valves are Model 8360 available from Spraying Systems Company. In the preferred embodiment of the invention, the check valves open when the pressure of the fluid within the fluid conduit 60 exceeds between 5 and 7 psi. Thus, when the pressure of the liquid within the fluid conduit 60 falls below the threshold value, the diaphragm check valve prevents liquid from being discharged through the associated nozzle 68. In the embodiment of the invention illustrated in FIG. 3, each nozzle 68 includes a spray tip that delivers flat, angular spray patterns, although other spray patterns are contemplated.

Referring back to FIG. 2, the cart enclosure 12 includes a motion detector 74 mounted to the top wall 24 and positioned to detect the shopping cart 54 as the shopping cart 54 enters the cart enclosure 12. The motion detector 74 generates a detection signal upon detecting movement beneath the motion detector 74. As will be described in detail below, upon detection of the shopping cart 54, the motion detector 74 sends a signal that opens a control valve to supply a pressurized source of sanitizing fluid to the spray arch 58. Although the present invention is shown as utilizing a motion detector 74 to detect the movement of the cart 54 into the enclosure 12, it is contemplated that other types of sensors could be utilized while operating within the scope of the invention. As an example, the motion detector 74 could be replaced by a through beam sensor operable to detect when a portion of the shopping cart enters the enclosure and breaks the sensor beam.

As illustrated in FIG. 1, the shopping cart enclosure 12 further includes a drain 76 mounted to the floor 14. The drain 76 includes a drain opening 78 (FIG. 1) that receives the excess fluid applied to the shopping cart and directs the excess fluid to a drain tube 79 (FIG. 2). The drain tube 79 can be connected to a drain hose such that the used sanitizing fluid can be fed to a discharge location, such as a sewer or drain.

Figure 4:
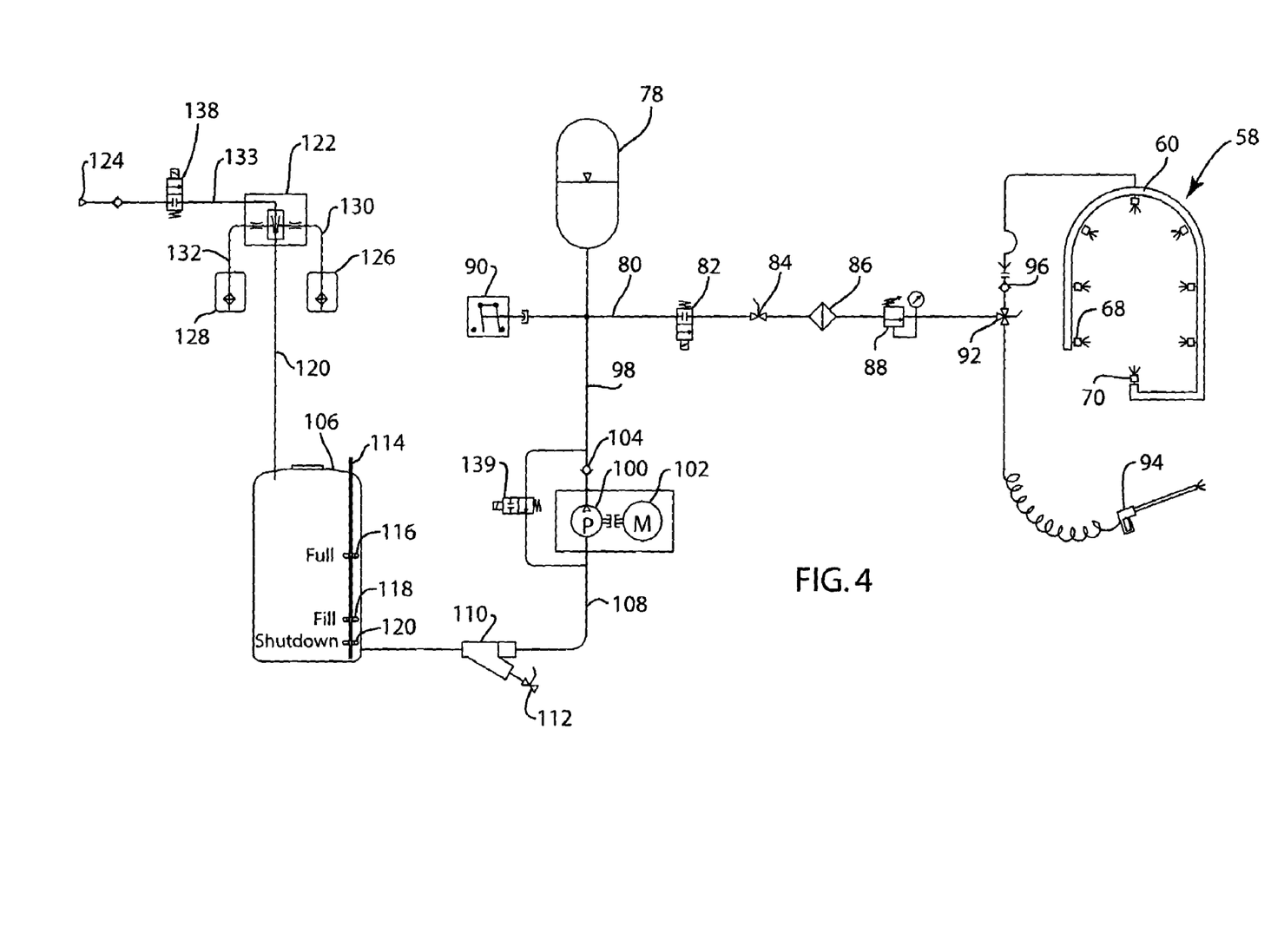
FIG. 4 is a fluid flow diagram illustrating the creation of the sanitizing fluid and the application of the sanitizing fluid through the spray arch and manual spray wand.

Referring now to FIG. 4, the fluid flow system and circuit for the cart sanitizing system of the present invention will be described. As illustrated, the fluid conduit 60 of the spray arch 58 is shown including the spray nozzles 68 and the floor mounted nozzle 70. The spray arch 58 is supplied with a pressurized source of sanitizing fluid from a pressure tank 78 through the fluid conduit 80. The fluid conduit 80 includes a control valve 82 that is automatically operated between an open and a closed position. Specifically, the control valve 82 is moved to its on, open position when the motion detector detects the movement of the shopping cart into the cart enclosure. The control valve 82 is moved to its closed, off position by a timer (not shown) upon the expiration of a spray period. In this manner, the control valve 82 controls the supply of pressurized sanitizing fluid to the spray arch 58.

In addition to the control valve 82, the fluid conduit 80 includes the manual shutoff valve 84, an inline strainer 86 and a pressure reducing valve 88. The pressure reducing valve 88 reduces the pressure from the pressure tank 78 down to a constant, selected value. In the embodiment of the invention illustrated, the pressure reducing valve 88 reduces the pressure of the sanitizing fluid to 40 psi. The charging of the pressure tank 78 is controlled by a pressure switch 90 to regulate the pressure within the tank to a range between 40 and 60 psi.

The fluid conduit 80 further includes a selection valve 92 that is operable to divert the flow of pressurized sanitation fluid between either the spray arch 58 or a manual spray wand 94. When the pressurized fluid is diverted to the manual spray wand 94, a user can spray the sanitizing fluid onto carts when the carts are not contained within the cart enclosure. A check valve 96 prevents the reverse flow of fluid from the spray arch 58.

The pressure tank 78 has a fifteen gallon capacity and is fed with sanitizing fluid through a filling conduit 98 by a pump 100 driven by motor 102. The operation of the pump 100 and motor 102 is controlled by the pressure switch 90 such that the pressure within the pressure tank is maintained between 40 and 60 psi. In the embodiment of the invention illustrated, the pump 100 is a magnetic driven, positive displacement pump with a capacity of approximately 2.2 gpm at 40 to 60 psi. A check valve 104 prevents the reverse flow of fluid within the filling conduit 68.

As illustrated in FIG. 4, the sanitizing fluid used to fill the pressure tank 78 is drawn from a bulk storage tank 106 through the make-up conduit 108. The make-up conduit 108 includes a strainer 110 having a manual drain 112. As the pressure tank 78 discharges fluid to the spray arch 58, the make-up fluid is supplied to the pressure tank 78 by the pump 100 through the make-up conduit 108 from the storage tank 106. In the embodiment of the invention illustrated, the storage tank 106 is a 75 gallon tank having a sensing probe 114. The sensing probe 114 includes three sensors for detecting the level of fluid within the storage tank 106. The first sensor 116 defines a maximum fill level for the storage tank 106. The second sensor 118 defines a lower level for the liquid within the tank, while the third sensor 120 is a shutdown sensor that prevents operation of the system should the liquid level within the storage tank 106 fall below this absolute minimum.

The storage tank 106 is fed with the sanitizing fluid by the fluid conduit 120. The fluid conduit 120 receives the sanitizing fluid from a mixing device 122. The mixing device 122 receives a supply of fresh water from fresh water inlet 124 and injects a surfactant from a surfactant tank 126 and a sanitizing agent from a chemical tank 128. In the embodiment of the invention illustrated, the surfactant tank 126 is a one gallon capacity tank while the chemical tank 128 has a five gallon capacity. The surfactant tank 126 is in fluid communication with the mixing device 122 by a surfactant tube 130, while the chemical tank 128 is in fluid communication with the mixing device 122 through a chemical tube 132.

Figure 7:
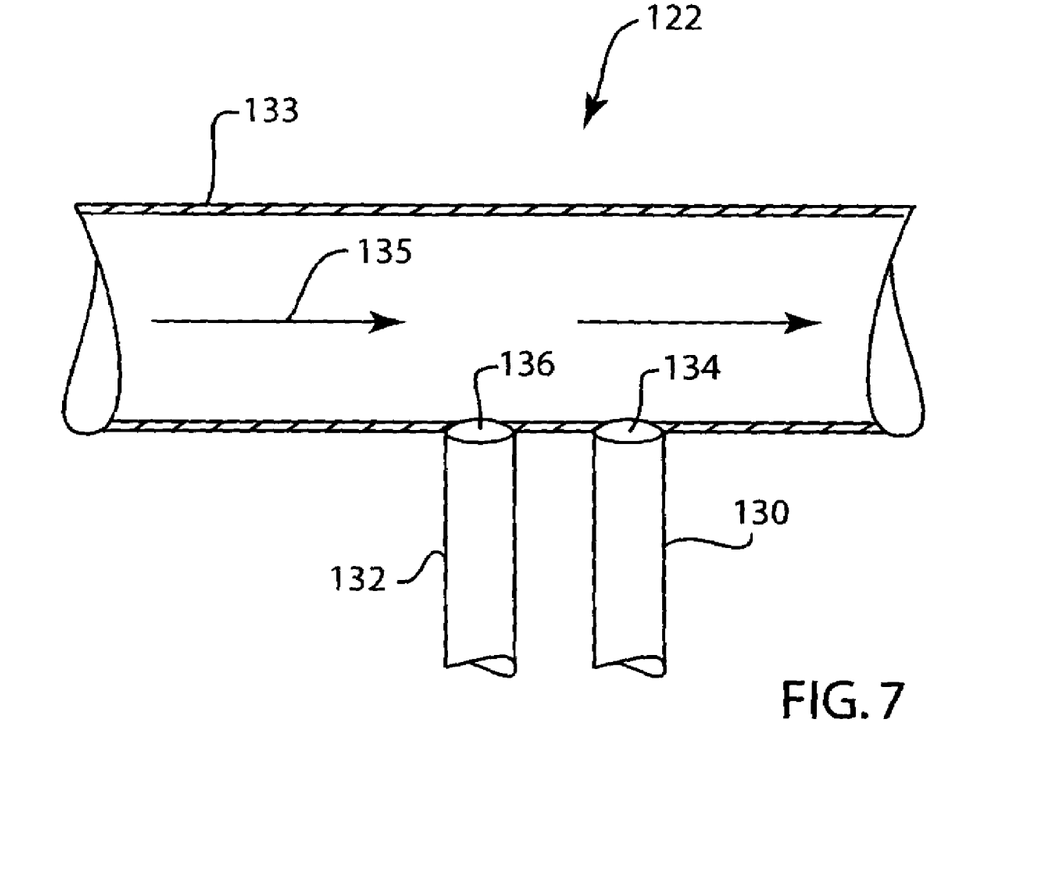
FIG. 7 is a schematic illustration of the chemical make-down system of the present invention.

Referring now to FIG. 7, thereshown is a schematic illustration of the mixing device 122. The mixing device 122 includes a fresh water conduit 133 that receives the flow of fresh water from the inlet. As the flow of fresh water 135 flows through the fresh water conduit 133, the flow of water passes over an inlet opening 134 of the surfactant tube 130 and an inlet opening 136 of the chemical tube 132. As the flow of fresh water 135 passes over the inlet openings 134 and 136, the flow of fresh water draws both the surfactant and the sanitizing agent into the fresh water conduit 133. In this manner, the mixing device 122 creates the desired mixture for the sanitizing fluid as it exits the mixing device 122 and is supplied to the storage tank 106.

The concentration of both the surfactant and the sanitizing agent within the sanitizing fluid is controlled by the diameter of the inlet openings 134 and 136. Thus, to modify the amount of either the surfactant or the sanitizing agent within the sanitizing fluid, the diameter of the inlet openings 134,136 can be modified. Preferably, the inlet openings 134,136 are contained in replaceable sections of the surfactant tube 130 and the chemical tube 132. Thus, the replaceable sections of the tubes can be modified if the concentration of the sanitizing fluid needs to be changed based upon the types of chemicals being used.

Referring back to FIG. 4, a water fill valve 138 is positioned to control the flow of fresh water through the fresh water conduit 133. The water fill valve 138 is operatively connected to the first sensor 116 and the second sensor 118. Thus, when the level of fluid within the storage tank 106 rises above the first sensor 116, the water fill valve 138 is closed to present any further supply of the sanitizing fluid. Likewise, when the liquid level in the tank 106 falls below the second sensor 118, the water fill valve 138 is opened to create an additional supply of the sanitizing fluid. As can be easily understood by the above description, the mixing device 122 creates the sanitizing fluid as the sanitizing fluid is required to fill the storage tank 106. Thus, the sanitizing fluid is created on the fly and only when desired.

In the preferred embodiment of the invention, the sanitizing fluid includes both the surfactant from the surfactant tank 126 and the sanitizing agent from the chemical tank 128. The surfactant functions to reduce the surface tension of the fresh water supply such that when the sanitizing fluid is applied to the shopping cart, the sanitizing fluid resists beading and dries more quickly. The sanitizing agent is selected in accordance with the present invention to provide a high level of sanitation to the shopping cart. In a preferred embodiment of the invention, the sanitizing liquid is a chemical agent that has been found to be food safe and does not require rinsing from the shopping carts. However, other types of sanitizing agents could be utilized while operating within the scope of the present invention.

When the cart sanitizing system shown in FIG. 4 is turned off, the dump valve 139 is opened such that the pressurized supply of sanitizing fluid from the pressure tank 78 is discharged into the storage tank 106. As illustrated in FIG. 4, the position of the first sensor 116 is selected such that when the storage tank 106 is filled to its maximum height, the storage tank 106 can still accept the full volume of the pressure tank 78.

Figure 5:
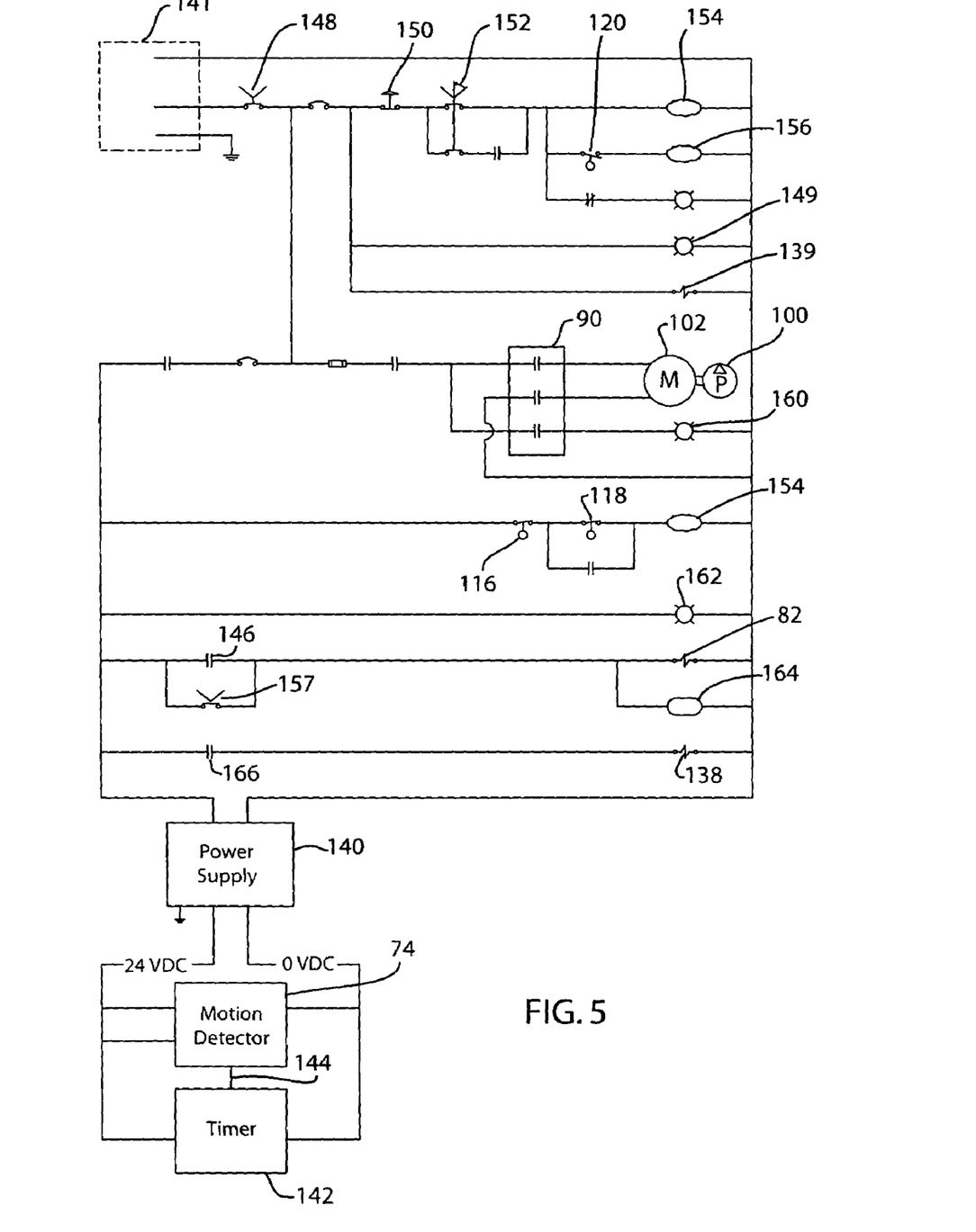
FIG. 5 is a schematic control diagram of the sanitizing system.

Referring now to FIG. 5, thereshown in an electrical wiring diagram for the sanitizing system of the present invention. The electrical system includes a power supply 140 coupled to a line voltage 141 to provide a 24 volt DC output to the motion detector 74 and a timer 142. As described previously, when the motion detector 74 detects the presence of a shopping cart, the motion detector 74 provides a signal along line 144 to the timer 142. Upon receiving the signal from the motion detector 74, the timer 142 begins counting down a spray period and closes the relay 146, thus opening the control valve 82. In the preferred embodiment of the invention, the spray period has a duration of thirty seconds, although other durations could be selected. The relay 146 remains closed until the spray period defined by the timer 142 expires. Once the spray period expires, the relay 146 is opened and the control valve 82 is closed.

As shown in FIG. 5, the electrical control circuit includes a main power switch 148, emergency stop switch 150, and a key switch 152. When any one of these three components are in the off position, power is interrupted to the master relays 154 and 156 of the control circuit.

When the main power switch 148 is moved to the on position, the power light 149 is illuminated. At the same time, the ready light 162 is also illuminated indicating that the system is ready for operation.

When the pressure switch 90 determines that the pressure tank is below the minimum pressure, the pressure switch 90 operates motor 102 to drive pump 100. When the motor and pump are being driven, the pump cycling light 160 is illuminated.

A spray selection switch 157 is position in parallel with the relay 146. The spray selection switch can be operated between an auto position and an on position. When the spray selection switch 157 is in the auto position, the relay 146 controls the activation of the control valve 82. When the spray selection switch 157 is in the on position, the control valve 82 supplies pressurized fluid to the spray arch continuously, regardless of whether a shopping cart is within the cart enclosure. Counter 164 is used to track the amount of time that the system is supplying sanitizing fluid.

The water fill valve 138 is coupled to the supply of power by relay 166. The relay 166 is part of the master control relay 154. When the first sensor 116 senses fluid, the normally close contact opens to prevent power from being supplied to the relay 156, thus interrupting power to the water fill valve 138, thus closing the water fill valve 138. Likewise, when the water level falls below the second sensor 118, the sensor 118 allows power to be supplied to the relay 154, which opens the water fill valve 138 to create an additional supply of the sanitizing fluid.

Figure 6:
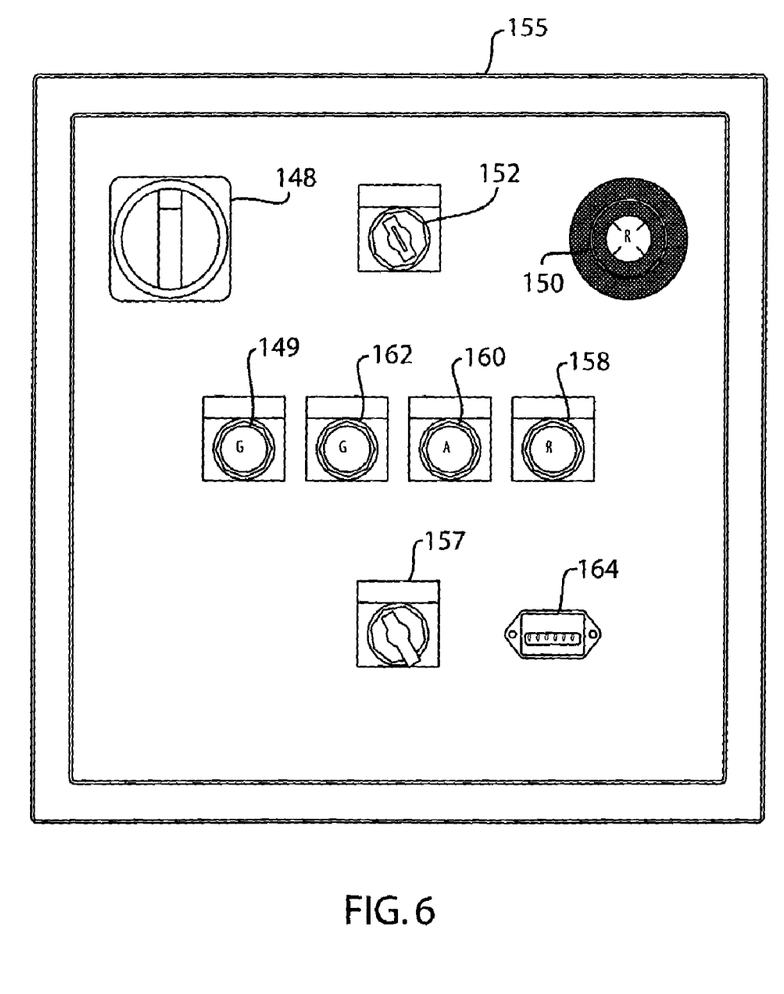
FIG. 6 is a front view of the control panel utilized to operate the sanitizing system.

Referring now to FIG. 6, thereshown is a view of the control panel of the cart sanitizing system of the present invention. The control panel includes the main power switch 148, the emergency stop switch 150, and the keyed switch 152. The spray selection switch 157 allows the user to select between an auto position that supplies special fluid to the spray arch upon detection of the cart by the motion detector as well as an on position. When the switch 157 is in the on position, pressurized fluid is supplied through the spray arch continuously regardless of whether a shopping cart is within the cart enclosure. The control panel 155 further includes an indicator light 158 indicating a low level of fluid within the supply tank, an indicator 160 indicating the pump is being cycled, and the ready light 162. The counter 164 is included on the control panel to indicate the amount of time the sanitizing system has been in used.

As the present invention may be embodied in several forms without departing from the spirit or essential characteristics thereof, it should also be understood that the above described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalents of such metes and bounds are therefore intended to be embraced by the appended claims.

Various alternatives and embodiments are contemplated as being within the scope of the following claims particularly pointing out and distinctly claiming the subject matter regarded as the invention.

What is claimed is:

1. A mobile sanitizing system for applying a sanitizing fluid to a shopping cart to sanitize the shopping cart, comprising:
   a cart enclosure for receiving the shopping cart, the cart enclosure including a floor, a pair of spaced side walls, an entrance and an exit;
   a single spray arch positioned in the enclosure between the entrance and the exit, the single spray arch having a plurality of spray nozzles positioned to direct the sanitizing fluid onto the shopping cart when the shopping cart is within the cart enclosure;
   a pressure tank coupled to the single spray arch, the pressure tank being operable to provide a pressurized supply of the sanitizing fluid to the single spray arch;
   a chemical make-down system coupled to the pressure tank to create the sanitizing fluid and supply the sanitizing fluid to the pressure tank, the chemical make-down system comprising:
      a surfactant tank including a supply of a surfactant;
      a chemical tank including a supply of a sanitizing agent; and
      a mixing device in fluid communication with a supply of water, the surfactant tank and the chemical tank and operable to mix a desired amount of the surfactant and a desired amount of the sanitizing agent into the supply of water to create the sanitizing fluid; and
   a drain positioned to receive the sanitizing fluid after the sanitizing fluid has been applied to the shopping cart, wherein the drain is coupled to a discharge tube to dispose of the sanitizing fluid.

2. The sanitizing system of claim 1 wherein the mixing device includes a surfactant tube coupled to the surfactant tank and a chemical tube coupled to the chemical tank wherein the supply of water passes over an inlet opening of the surfactant tube and an inlet opening of the chemical tube to draw the surfactant and the sanitizing agent into the flow of water.

3. The sanitizing system of claim 1 further comprising a manual wand coupled to the pressure tank by a selection valve, wherein the selection valve is operable to divert the pressurized supply of sanitizing fluid between the manual wand and the spray arch.

4. The sanitizing system of claim 1 wherein the cart enclosure further comprises:
   a pair of rear wheels positioned near the entrance;
   a pair of non-skid pads positioned near the exit, wherein the floor slopes downward from the entrance to the exit;
   an entrance ramp movable between a storage position and a loading position in which the entrance ramp extends between the floor and the ground, the entrance ramp having a pair of adjustable guide rails to guide the shopping cart toward the entrance; and
   an exit ramp movable between a storage position and a loading position in which the entrance ramp extends between the floor and the ground, the entrance ramp having a pair of guide rails to guide the shopping cart from the exit toward the ground.

5. The sanitizing system of claim 2 wherein the inlet openings for both the surfactant tube and the chemical tube are selectable to vary the concentration of the sanitizing fluid.

6. The sanitizing system of claim 2 further comprising a storage tank positioned to receive the sanitizing fluid from the mixing device, the storage tank being in fluid communication with the pressure tank to provide the sanitizing fluid to the pressure tank, the storage tank having a fill sensor to detect when the level of the sanitizing fluid in the storage tank falls below a lower level, wherein the fill sensor activates a water fill valve to provide the supply of water to the mixing device.

7. The sanitizing system of claim 6 further comprising a pressure pump positioned to pump the sanitizing fluid from the storage tank to the pressure tank, wherein the pressure pump is activated to charge the pressure tank when the pressure in the pressure tank falls below a minimum pressure.

8. A mobile sanitizing system for applying a sanitizing fluid to a shopping cart to sanitize the shopping cart, comprising:

a cart enclosure for receiving the shopping cart, the cart enclosure including a floor, a pair of spaced side walls, an entrance and an exit;

a single spray arch positioned in the enclosure between the entrance and the exit, the single spray arch having a plurality of spray nozzles positioned to direct the sanitizing fluid onto the shopping cart when the shopping cart is within the cart enclosure;

a pressure tank coupled to the single spray arch, the pressure tank being operable to provide a pressurized supply of the sanitizing fluid to the single spray arch;

a detector mounted within the enclosure to detect the entrance of a shopping cart into the cart enclosure, wherein the pressure tank provides the pressurized supply of sanitizing fluid to the single spray arch upon detection of the shopping cart;

a chemical make-down system coupled to the pressure tank to create the sanitizing fluid and supply the sanitizing fluid to the pressure tank, the chemical make-down system comprising:

a surfactant tank including a supply of a surfactant;

a chemical tank including a supply of a sanitizing agent; and a mixing device in fluid communication with a supply of water, the surfactant tank and the chemical tank and operable to mix a desired amount of the surfactant and a desired amount of the sanitizing agent into the supply of water to create the sanitizing fluid; and a drain positioned to receive the sanitizing fluid after the sanitizing fluid has been applied to the shopping cart, wherein the drain is coupled to a discharge tube to dispose of the sanitizing fluid.

9. The sanitizing system of claim 8 wherein the mixing device includes a surfactant tube coupled to the surfactant tank and a chemical tube coupled to the chemical tank, wherein the supply of water passes over an inlet opening of the surfactant tube and an inlet opening of the chemical tube to draw the surfactant and the chemical agent into the flow of water.

10. The sanitizing system of claim 8 further comprising a storage tank positioned to receive the sanitizing fluid from the mixing device, the storage tank being in fluid communication with the pressure tank to provide a sanitizing fluid to the pressure tank, the storage tank having a fill sensor operable to detect when the level of the sanitizing fluid in the storage tanks falls below a lower level, wherein the fill sensor activates a water fill valve to provide the supply of water to the mixing device to create an additional supply of sanitizing fluid to fill the storage tank.

11. The sanitizing system of claim 8 wherein the cart enclosure further comprises:

a pair of rear wheels positioned near the entrance;

a pair of non-skid pads positioned near the exit, wherein the floor slopes downward from the entrance to the exit;

an entrance ramp movable between a storage position and a loading position in which the entrance ramp extends between the floor and the ground, the entrance ramp having a pair of adjustable guide rails to guide the shopping cart toward the entrance; and an exit ramp movable between a storage position and a loading position in which the entrance ramp extends between the floor and the ground, the entrance ramp having a pair of guide rails to guide the shopping cart from the exit toward the ground.

12. The sanitizing system of claim 9 wherein the inlet openings for both the surfactant tube and the chemical tube are selectable to vary the concentration of the sanitizing fluid.

13. The sanitizing system of claim 10 further comprising a pressure pump positioned to pump the sanitizing fluid from the storage tank to the pressure tank, wherein the pressure pump is activated to charge the pressure tank when the pressure within the pressure tank falls below a minimum pressure.

14. The sanitizing system of claim 13 wherein the spray nozzles positioned on the spray arch each include a diaphragm check valve that opens to provide a spray pattern of the sanitizing fluid only when the pressure of the sanitizing fluid exceeds a threshold pressure.

15. A method of sanitizing a shopping cart, the method comprising the steps of:

providing a cart enclosure having an entrance, an exit, a drain coupled to a discharge tube and a single spray arch positioned between the entrance and the exit, the single spray arch having a plurality of spray nozzles;

moving at least one shopping cart through the entrance;

creating a supply of a sanitizing fluid, including the steps of:

passing a flow of water through a mixing device;

drawing a selected amount of a surfactant into the flow of water;

drawing a selected amount of a sanitizing agent into the water such that the mixture of the water, sanitizing agent and surfactant creates the sanitizing fluid having the selected amount of the surfactant and the sanitizing agent;

providing a pressurized supply of the sanitizing fluid to the single spray arch such that each of the nozzles directs a spray of the sanitizing fluid onto the shopping cart; and draining the sanitize fluid away from the cart enclosure through the drain and discharge tube such that the sanitizing fluid is only applied to the shopping carts a single time.

16. The method of claim 15 wherein a plurality of shopping carts are pushed through the entrance opening nested together.

17. The method of claim 15 further comprising the steps of removing the cart from the enclosure and allowing the cart to dry without rinsing.

18. The method of claim 15 wherein the spray nozzles direct the spray of sanitizing fluid onto the shopping cart only when the pressure of the sanitizing fluid exceeds a threshold pressure.

* * * * *